US012799234B2

(12) United States Patent
Huang et al.

(10) Patent No.: US 12,799,234 B2
(45) Date of Patent: Nov. 17, 2026

(54) USE OF FUNCTIONAL MONOMERS IN EMULSION POLYMERIZATION

(71) Applicants: CHANGZHOU UNIVERSITY, Changzhou (CN); CHANGSHU KANGSHIDE DECORATION MATERIALS TECHNOLOGY CO., LTD., Suzhou (CN)

(72) Inventors: Wenyan Huang, Changzhou (CN); Ying Zhou, Changzhou (CN); Li Jiang, Changzhou (CN); Bibiao Jiang, Changzhou (CN); Jianxin Zhang, Suzhou (CN); Qimin Jiang, Changzhou (CN); Hongjun Yang, Changzhou (CN); Xiaoqiang Xue, Changzhou (CN)

(73) Assignees: CHANGZHOU UNIVERSITY, Changzhou (CN); CHANGSHU KANGSHIDE DECORATION MATERIALS TECHNOLOGY CO., LTD., Suzhou (CN)

( * ) Notice: Subject to any disclaimer, the term of this patent is extended or adjusted under 35 U.S.C. 154(b) by 492 days.

(21) Appl. No.: 18/516,903

(22) Filed: Nov. 21, 2023

(65) Prior Publication Data

US 2024/0199769 A1 Jun. 20, 2024

Related U.S. Application Data

(63) Continuation of application No. PCT/CN2023/077119, filed on Feb. 20, 2023.

(30) Foreign Application Priority Data

Dec. 13, 2022 (CN) ........................ 202211593277.0

(51) Int. Cl.

| | |
|---|---|
| ***C08F 2/30*** | (2006.01) |
| ***C07C 233/09*** | (2006.01) |
| ***C08F 4/40*** | (2006.01) |
| ***C08F 6/22*** | (2006.01) |
| ***C08F 212/08*** | (2006.01) |
| ***C08F 220/06*** | (2006.01) |
| ***C08F 220/18*** | (2006.01) |

(52) U.S. Cl.

CPC .............. *C08F 2/30* (2013.01); *C07C 233/09* (2013.01); *C08F 4/40* (2013.01); *C08F 6/22* (2013.01); *C08F 212/08* (2013.01); *C08F 220/06* (2013.01); *C08F 220/18* (2013.01); *C08F 2400/02* (2013.01)

(58) Field of Classification Search

CPC ...... C08F 2/30; C08F 4/40; C08F 6/22; C08F 212/08; C08F 220/06; C08F 220/18; C08F 2400/02; C08F 2/28; C08F 6/14; C08F 12/08; C08F 220/14; C08F 220/20; C08F 222/38; C07C 233/09

USPC .......................................................... 524/458

See application file for complete search history.

(56) References Cited

U.S. PATENT DOCUMENTS

| | | | |
|---|---|---|---|
| 2003/0164476 A1 | 9/2003 | Guo et al. | |
| 2022/0144986 A1 | 5/2022 | Huang et al. | |
| 2023/0018276 A1 | 1/2023 | Huang et al. | |
| 2023/0028363 A1 * | 1/2023 | Huang | .................... C07C 67/08 |

FOREIGN PATENT DOCUMENTS

| | | |
|---|---|---|
| CN | 106496398 A | 3/2017 |
| CN | 109529714 A | 3/2019 |
| CN | 111302960 A | 6/2020 |
| JP | S62121792 A | 6/1987 |

OTHER PUBLICATIONS

International Search Report in PCT/CN2023/077119 mailed on May 18, 2023, 6 pages.

Written Opinion in PCT/CN2023/077119 mailed on May 18, 2023, 7 pages.

First Office Action in Chinese Application No. 202211593277.0 mailed on Dec. 16, 2024, 16 pages.

Kobehoo, "[Help] Question about the hydrophilicity of each-hydrophilic group", Web Page<https://muchong.com/html/201009/2448995.html>, Sep. 30, 2010.

* cited by examiner

*Primary Examiner* — Hannah J Pak

(74) *Attorney, Agent, or Firm* — METIS IP LLC

(57) ABSTRACT

The present disclosure discloses a method of a functional monomer in emulsion polymerization, belonging to the field of synthesis of functional monomers and methods of emulsion polymerization. The present disclosure obtains functional monomers TDMAMA and TDMAIA by synthesis, which may show different functions at different pH. By adjusting an $H^+/OH^-$ content in an emulsion with an acid and alkali solution at a certain concentration, it is found that the functional monomers are both an emulsifier, a polymerizing monomer, and a reducing agent at a specific pH, at which the emulsion is stable, and may perform free-radical emulsion polymerization at room temperature, and high molecular weight polymer is obtained through a branched polymerization. When an $H^+$ concentration is less than $OH^-$, the emulsion is unstable and has flocculation, then the polymerization terminates, and emulsion breaking can be realized without adding an additional emulsion breaker.

9 Claims, 3 Drawing Sheets

USE OF FUNCTIONAL MONOMERS IN EMULSION POLYMERIZATION

CROSS REFERENCE TO RELATED APPLICATIONS

The present disclosure is a continuation of International Patent Application No. PCT/CN2023/077119, filed on Feb. 20, 2023, which claims priority to Chinese Patent Application No. 202211593277.0, filed on Dec. 13, 2022, the entire contents of which are hereby incorporated by reference.

TECHNICAL FIELD

The present disclosure belongs to the field of design and preparation of functional monomers in polymer chemistry and emulsion polymerization, and in particular, to the synthesis of a reactive $H^+/OH^-$ responsive functional monomer and a method of emulsion polymerization at room temperature.

BACKGROUND

A reactive emulsifier is a monomer having an emulsifying function and is capable of participating in a polymerization reaction. A conventional non-reactive emulsifier mainly relies on physical adsorption to aggregate on a surface of emulsion particles, and thus the adsorption of the emulsifier is destroyed when subjected to an external force, resulting in the destabilization of an emulsion. In contrast, the reactive emulsifier is bonded to the surface of emulsion particles in the form of covalent bonds and is not easily affected by the external force. Its reactivity not only stabilizes the emulsion but also prevents the emulsifier from migrating to a surface of a film during film formation, resulting in a loss of performance. It is suitable for the production of water-resistant coatings. According to its reactive group, the reactive emulsifier may be categorized as allyl-type, styrene-type, acrylic acid-type, acrylamide-type, etc. Depending on a type of its hydrophilic group, it may be categorized as anionic-type, cationic-type, and nonionic-type.

The cationic-type reactive emulsifier has a cationic hydrophilic group and is mostly of a quaternary ammonium salt type. A synthesis condition of the quaternary ammonium salt type emulsifier is more complex, it is generated by tertiary amines and halogenated alkanes under a certain condition, and if it is used as the emulsifier, a polymerization reaction is difficult to carry out at room temperature. A structure of the tertiary amines before quaternization is a special structure with multiple functions. Chinese patent application No. CN202010242562.2, entitled "A polymerizable surfactant with reducing properties and a preparation method thereof", discloses the synthesis of a polymerizable surfactant with reducing properties, which requires the addition of sodium bicarbonate during an emulsion polymerization, and the polymerizable surfactant has excellent emulsifying properties when a pH of the polymerizable surfactant is weakly alkaline, and can also act as a reducing agent to participate in a redox initialization reaction. A one-step method of emulsion polymerization may be carried out at room temperature or low temperature to obtain an environment-friendly emulsion with a branched structure. As the inventor studied more deeply, it was found that the monomer's reducing properties are poor, and it has not been studied how to realize a multifunctional conversion, and it is necessary to add an additional emulsion breaker to collect a polymer after the reaction. Although it is well known in the field that a tertiary amine group is reductive, in a practical application, an emulsifier containing the tertiary amine group is difficult to use as the reducing agent and has poor reducing properties. Moreover, the emulsion obtained after the polymerization reaction is very stable, and it is necessary to add an additional emulsion breaker when breaking the emulsion.

To address this problem, the present disclosure provides a functional monomer and use thereof in emulsion polymerization, which regulates an H/OH content by introducing acid and alkali solutions, and regulates its different functions in the emulsifier, polymerizing monomer, reducing agent, emulsion breaker, etc. at different pH, providing a new idea of regulatability of the emulsion polymerization.

SUMMARY

In response to the above problems, the present disclosure aims to provide an $H^+/OH^-$ functional monomer and a use thereof in emulsion polymerization. By adjusting an $H^+$ and OH concentration in a functional monomer solution, it may have different roles such as an emulsifier, polymerizing monomer, and reducing agent in different pH systems. For example, it may be used as the emulsifier, polymerizing monomer, and reducing agent at a specific pH ($5.0 \leq pH < 7.0$). When used as the reducing agent, the functional monomer and an initiator with oxidizing properties form a redox initiation system, so as to initialize rapid polymerization at room temperature (5~35° C.), and ultimately obtain a high molecular weight polymer with a certain branched structure. In a stable polymer emulsion system, the reaction may be terminated directly by increasing an $OH^-$ content in the emulsion, without needing to add an additional emulsion breaker.

In order to realize the above objects, the present disclosure adopts a following technical solution.

An $H^+/OH^-$ responsive functional monomer is provided, and a structure of the functional monomer is shown as:

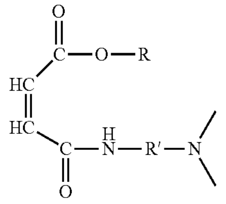

or

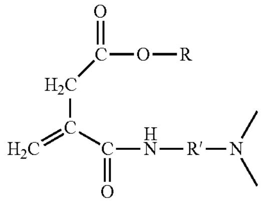

wherein R, R' are long-chain aliphatic hydrocarbon structures of different lengths.

Further, the functional monomers are 2-(tetradecyl ester) dimethylaminoacetamide maleate (TDMAMA) and/or 2-(tetradecyl ester) dimethylaminoacetamide itaconic acid (TDMAIA).

A structural formula of TDMAMA is:

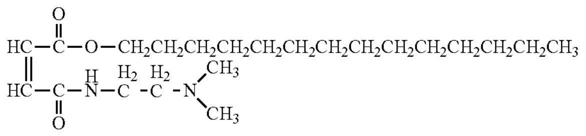

A structural formula of TDMAIA is:

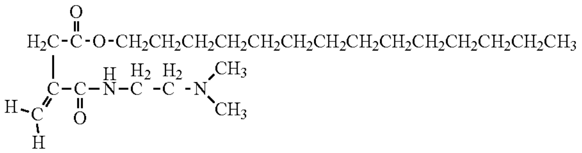

The $H^+/OH^-$ responsive functional monomer may have different roles in different pH systems.

The $H^+/OH^-$ responsive functional monomer, by adjusting an $H^+$ or $OH^-$ concentration in a functional monomer water solution, has different roles at different pH: when pH<3.0, the functional monomer is only used as an emulsifier; when 3.0≤pH<5.0, the functional monomer is used as both an emulsifier and a polymerizing monomer; when 5.0≤pH<7.0, the functional monomer is used as an emulsifier, a polymerizing monomer, and a reducing agent; when 7.0≤pH<8.0, the functional monomer is only used as both a reducing agent and a polymerizing monomer; and when pH≥8.0, the functional monomer is used as an emulsion breaker; the functional monomer, when used as the emulsifier, has a critical micelle concentration (CMC) of 0.0023 mol/L-1-0.0035 mol/$L^{-1}$; and the room temperature is an environmental temperature of 5° C.-35° C. in a laboratory.

Further, the stability of the functional monomer water solution was regulated using different pH regulators. The functional monomer (TDMAMA or TDMAIA) was dissolved in deionized water containing a pH regulator at room temperature, and then a vinyl monomer was added and stirred to form a white emulsion, and when an $H^+$ concentration in the emulsion was greater than an $OH^-$ concentration, the $H^+$ was able to combine with a tertiary amine structure of an emulsifier monomer in the form of ionic bonds to form a stable emulsion, then an oxidizing agent was added to the emulsion, the emulsion was stirred at room temperature to be blue, then the emulsion was stirred for more than 4 hours, and high molecular weight polymer is obtained, increasing an $OH^-$ content in a stable polymer emulsion within a required reaction time can terminate the polymerization reaction, and the polymer can be precipitated directly by sedimentation; the functional monomer may also form a redox initiation system with an initiator with oxidizing properties and initialize rapid polymerization at room temperature, so as to obtain high molecular weight polymer with a certain branched structure.

A specific process of the emulsion polymerization is as follows: weighing an $H^+/OH^-$ regulator and dissolving it in deionized water, adding the functional monomer, stirring it until it is dissolved to obtain a mixed solution; controlling a pH of the mixed solution to 5.0≤pH<7.0 through an amount of acid; adding a vinyl monomer and stirring to make it a uniform white emulsion; then pre-emulsifying the emulsion, stirring in an ice bath, deoxidizing, and venting with argon gas; after deoxidation, adding persulfate in the presence of argon gas; at this time the emulsion is stable and blue, after the emulsion polymerization reaction at room temperature, adjusting the pH≥8.0 to terminate the emulsion polymerization reaction, obtaining polymer.

At room temperature, ultra-high molecular weight branched polymer was obtained through emulsion polymerization, and in a stable polymer emulsion system, the reaction may be terminated directly by increasing the $OH^-$ content in the emulsion (pH≥8.0) to realize the response of the emulsion to $H^+/OH^-$.

Further, the $H^+/OH^-$ regulator may include hydrochloric acid, glacial acetic acid, sodium hydroxide, sodium bicarbonate, or the like.

In a preferred technical solution, a molar ratio of the functional monomer to $H^+$ is 1:(0.25~1.0);

In a preferred technical solution, a molar ratio of the functional monomer to the vinyl monomer is (3~5):100;

In a preferred technical solution, the oxidizing agent is persulfate or the like;

In a preferred technical solution, the vinyl monomer is styrene, methacrylate, acrylic monomer, or the like;

In a preferred technical solution, a molar ratio of the functional monomer to the oxidizing agent is 5~10:1;

In a preferred technical solution, the room temperature for the emulsion polymerization is 5~35° C.;

In a preferred technical solution, the polymerization reaction time is 4~8 h;

In a preferred technical solution, when the emulsion polymerization system is blue, 3.0<pH<7.0;

In a preferred technical solution, the $OH^-$ concentration required for termination of the emulsion polymerization reaction is greater than the $H^+$ concentration; and In a preferred technical embodiment, pH is 6.0<pH<6.5 at which the monomer is used as the reducing agent by controlling an acid content.

Further, the addition of $H^+$ (5.0≤pH<7.0) not only enhances the hydrophilicity of the functional monomer, which enhances the emulsifying ability to a certain extent, but also synergistically promotes the reducing properties under a condition of 5.0≤pH<7.0, so that the emulsion formed by the functional monomer has a lower particle size and better stability, and is capable of initiating the polymerization reaction at room temperature or even at a low temperature. It has a high conversion rate, high molecular weight, and branched structure, and the whole polymerization reaction is simple, easy to operate, and can be carried out at room temperature, which can save energy and cost, and can be applied to the production of functional polymer on a large scale.

The present disclosure provides a polymer, wherein its preparation comprises:

- dissolving a functional monomer in a water solution containing a pH adjustor to obtain a mixed solution;
- controlling a pH of the mixed solution;
- adding a vinyl monomer and stirring to form emulsion; and
- adding an oxidizing agent to carry out emulsion polymerization and obtaining the polymer,
- wherein a structure of the functional monomer is shown as:

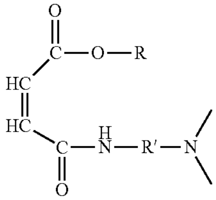

or

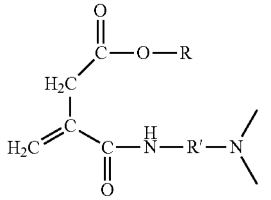

where R, R' are long-chain aliphatic hydrocarbon structures of different lengths.

When pH<3.0, the functional monomer is used as an emulsifier;

When 3.0≤pH<5.0, the functional monomer is used as an emulsifier and a polymerizing monomer;

When $5.0 \leq pH < 7.0$, the functional monomer is used as an emulsifier, polymerizing monomer and reducing agent;

When $7.0 \leq pH < 8.0$, the functional monomer is used as a reducing agent and a polymerizing monomer; and When $pH \geq 8.0$, the functional monomer is used only as an emulsion breaker (also referred to as demulsifier).

Advantages of the present disclosure are as follows:

1. A synthesis path of the reactive $H^+/OH^-$ emulsifier monomer in the method of the present disclosure is simple and has a high yield, and by applying it to emulsion polymerization, the regulation of the emulsion polymerization may be realized by adjusting an $H^+/OH^-$ content, so that the emulsion remains stable and undergoes a polymerization reaction under a condition of a high $H^+$ concentration, and the emulsion is flocculated and the reaction is terminated under a condition of a high $OH^-$ concentration.

2. The reactive $H^+/OH^-$ emulsifier monomer in the method of the present disclosure has a tertiary amine structure, and when a molar ratio of the tertiary amine structure to the $H^+$ is within the range of 1:0.25~1:1.0 ($5.0 \leq pH < 7.0$), it can initiate the emulsion polymerization reaction with the oxidizing agent at room temperature (5~35° C.) and achieve a high conversion rate and a high molecular weight in a short time. In addition, if the reaction system is acidic, namely, the pH value is less than 7, $H^+$ and tertiary amine can be complexed to form quaternary ammonium salt, methyl nitrogen protonated has the better initiation ability.

3. The reactive $H^+/OH^-$ emulsifier monomer in the method of the present disclosure is copolymerized with a polymerizing monomer, and can be applied to the preparation of branched polymer.

DETAILED DESCRIPTION

Figure 1:
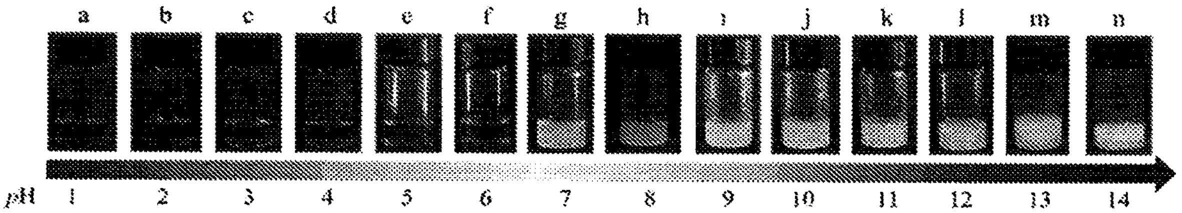
FIG. 1 illustrates an exemplary dissolution of an emulsifier monomer in water at different pH in Example 1.

Some embodiments of the present disclosure provide a functional monomer, a polymer, and a method of preparing the polymer using the functional monomer. A structure of the functional monomer is shown as:

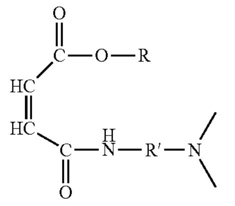

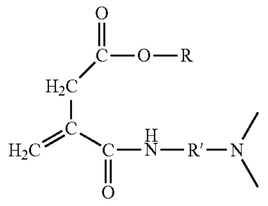

wherein R, R' are long-chain aliphatic hydrocarbon structures of different lengths.

In some embodiments, the functional monomer is an $H^+/OH^-$ responsive functional monomer. As used herein, the $H^+/OH^-$ responsive functional monomer refers to a functional monomer which have different functions in response to different pH.

In some embodiments, the functional monomer presents different functions at different pH by adjusting an $H^+$ or $OH^-$ concentration in a functional monomer water solution, when $pH < 3.0$, the functional monomer is used as an emulsifier; when $3.0 \leq pH < 5.0$, the functional monomer is used as both an emulsifier and a polymerizing monomer; when $5.0 \leq pH < 7.0$, the functional monomer is used as an emulsifier, a polymerizing monomer, and a reducing agent; when $7.0 \leq pH < 8.0$, the functional monomer is used as both a reducing agent and a polymerizing monomer; and when $pH \geq 8.0$, the functional monomer is only used as demulsifier.

The method of preparing the polymer using the functional monomer may include:

- weighing a pH regulator and dissolving it in water, adding the functional monomer to obtain a mixed solution;
- controlling a pH of the mixed solution;
- adding a vinyl monomer and stirring to form emulsion; and
- adding an oxidizing agent to carry out emulsion polymerization and obtaining the polymer.

In some embodiments, the pH regulator (also known as an $H^+/OH^-$ regulating agent) may include hydrochloric acid, glacial acetic acid, sodium hydroxide, sodium bicarbonate, or any other commonly-used pH regulators (e.g., malic acid).

In some embodiments, a molar ratio of the functional monomer to the vinyl monomer is in a range of 1:(0.1-1.2), or 1:(0.15-1.1), or 1:(0.2-1.0), or 1:(0.23-1.0), or 1:(0.25-1.0), or 1:(0.28-1.0), or 1:(0.28-0.8), etc.

In some embodiments, a molar ratio of the functional monomer to the vinyl monomer is in a range of (1-10):100, or (2-8):100, or (3-7): 100, or (3-6):100, or (3-5):100, or (3-4):100, etc.

In some embodiments, the vinyl monomer includes styrene monomer, methacrylate monomer, acrylic monomer, or the like, or any combination thereof.

In some embodiments, the functional monomer includes 2-(tetradecyl ester) dimethylaminoacetamide maleate or 2-(tetradecyl ester) dimethylaminoacetamide itaconic acid.

In some embodiments, the oxidizing agent includes persulfate, or any other oxidizing agents, e.g., potassium persulfate. In some embodiments, the persulfate includes sodium persulfate, etc.

In some embodiments, a molar ratio of the functional monomer to the oxidizing agent is in a range of (1-20):1, or (2-18):1, or (3-15):1, or (4-10):1, or (5-10):1, etc.

In some embodiments, a polymerization reaction time is 4-8 h; and the polymerization reaction is performed at room temperature of 5° C.-35° C.

Example 1: Preparation of Two Emulsifier Monomers

(1) Preparation of 2-(tetradecyl ester) dimethylaminoacetamide maleate (TDMAMA)

Figure 5:
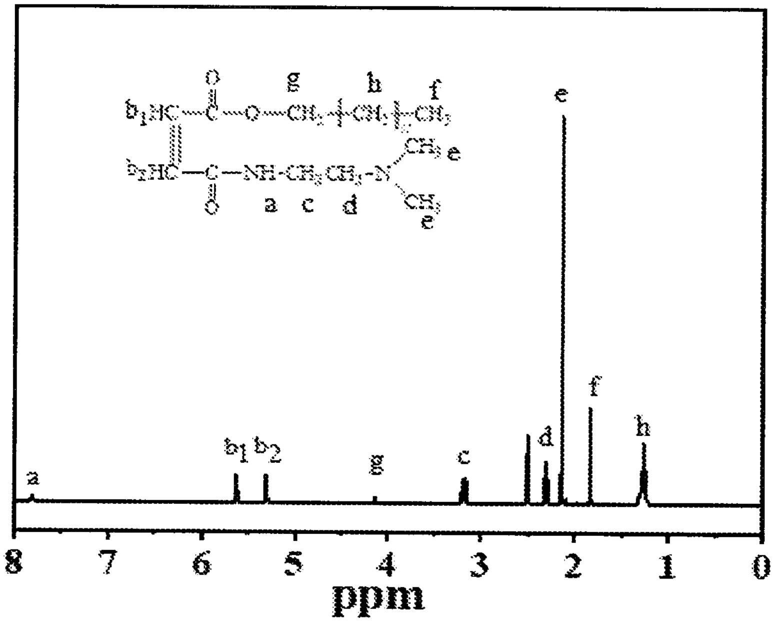
FIG. 5 illustrates an NMR hydrogen spectrum of 2-(tetradecyl ester) dimethylaminoacetamide maleate (TDMAMA).

Maleic anhydride (49.0302 g, 0.5 mol) was dissolved into 300 mL of chloroform and added to a three-necked flask equipped with a stirrer, a reflux condenser tube, and a constant-pressure dropping funnel, and p-toluenesulfonic acid (0.1502 g, 0.3%) was added to a reaction vessel as a catalyst after the flask had risen to 60° C. Then N, N-dimethylethylenediamine (44.0110 g, 0.5 mol) was dissolved into 100 mL of chloroform and slowly added dropwise into the reaction vessel, stirred, and refluxed for 2 h. After the reaction, it was cooled and crystallized at room temperature, and precipitate was filtered and recrystallized with 200 mL of ethanol two times, and then dried under vacuum to constant weight to obtain a white powder. A product obtained in the previous step (90.8010 g, 0.5 mol) was dissolved chloroform and was added to a three-necked flask with tetradecanol (10.8401 g, 0.06 mol), the flask was placed in a water bath at 80° C., and the reaction was stirred at reflux for 24 h. After the reaction, anhydrous sodium sulfate was added to a chloroform solution and dried overnight, the chloroform solution was passed through an alkaline alumina column, and the chloroform was removed by rotary evaporator at 30~40° C., and the product was obtained by vacuum drying. A purity was 95.3% as measured by high-performance liquid chromatography, and an NMR hydrogen spectrum is shown as in FIG. 5.

(2) Preparation of 2-(tetradecyl ester) dimethylaminoacetamide itaconic acid (TDMAIA)

Itaconic anhydride (56.0101 g, 0.5 mol) was dissolved into 300 mL of chloroform and added into a three-necked flask equipped with a stirrer, a reflux condenser tube, and a constant-pressure dropping funnel, then p-toluenesulfonic acid (0.1505 g, 0.3%) was added into a reaction vessel as a catalyst after the flask had risen to 60° C. Then N, N-dimethylethylenediamine (44.0115 g, 0.5 mol) was dissolved into 100 mL of chloroform and slowly added dropwise into the reaction vessel, stirred and refluxed for 2 h. After the reaction, it was cooled and crystallized at room temperature, and precipitate was filtered and recrystallized with 200 mL of ethanol two times, and then dried under vacuum to constant weight to obtain a white powder. A product obtained in the previous step (100.0231 g, 0.5 mol) was dissolved in a water solution of chloroform and tetradecanol (10.8407 g, 0.06 mol) was added to a three-necked flask, the flask was placed in a water bath at 80° C., and the flask was stirred at reflux for 24 h. After the reaction, anhydrous sodium sulfate was added to a chloroform solution and dried overnight, the chloroform solution was passed through an alkaline alumina column, and the chloroform was removed by rotary evaporator at 30~40° C., and the product was obtained by vacuum drying. A purity was 97.7% as measured by high-performance liquid chromatography.

Example 2: Dissolution of Emulsifier Monomer TDMAMA in a Water Solution at Different pH A 1 mol/L hydrochloric acid solution, glacial acetic acid solution, and sodium hydroxide solution were prepared and mixed in different proportions to form a water solution at a pH of 1~14. TDMAMA (0.0410 g, 0.12 mmol) prepared in Example 1 was weighed and added to 1.0 mL of a water solution at different pH respectively and dissolved by ultrasonic dispersion, and its dissolution was observed.

As shown in FIG. 1, the solution became turbid as pH increased. When an $H^+$ concentration was greater than $OH^-$ (pH<7.0), TDMAMA can be used as an emulsifier and can be completely dissolved in water, and when the $H^+$ concentration was less than or equal to $OH^-$, the emulsifier was poorly dissolved.

Example 3: Test of Stability of Emulsions Obtained with TDMAMA at Different pH

A 1 mol/L hydrochloric acid solution, a glacial acetic acid solution, and a sodium hydroxide solution were prepared and mixed in different proportions to form a water solution at a pH of 1~14. TDMAMA (0.3402 g, 0.96 mmol) prepared in Example 1 was weighed and added to 8.0 mL of a water solution at different pH respectively and dissolved by ultrasonic dispersion. After the dissolution was completed, styrene (2.0011 g, 0.019 mol) was weighed and added to the TDMAMA water solution prepared respectively, and emulsified by ultrasonication for 5 min and left to stand. An initial emulsion volume $V_0$ and a remaining emulsion volume V after 30 min of standing were recorded respectively, and an emulsion stability coefficient $V/V_0$ was calculated. The higher the emulsion stability coefficient, the better the emulsifying ability of the emulsifier and the more stable the emulsion.

Figure 2:
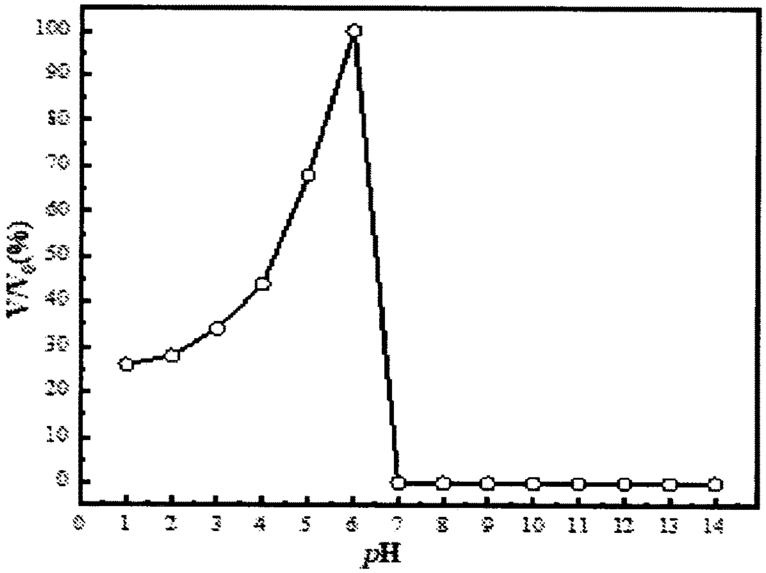
FIG. 2 illustrates an exemplary testing situation of the stability of an emulsion at different pH in Example 2.

As shown in FIG. 2, when an $H^+$ concentration was greater than $OH^-$ (pH<7.0), the emulsion stability was significantly better than that when the $H^+$ concentration was less than OH (pH≥7.0). The emulsion stability is better when 5<pH<7.0.

Example 4: Emulsion Polymerization Reaction

Dilute HCl (0.0953 g, 0.96 mmol) at a concentration of 37% was weighed and dissolved in deionized water (8.0021 g) and TDMAMA (0.3402 g, 0.96 mmol) was added. After stirring and leaving it to dissolve, a pH corresponding to a mixed water solution of a functional monomer and hydrochloric acid was measured to be 5.32. Styrene (2.0032 g, 0.019 mol, $m_{St}$:$m_{water}$=1:4) was weighed and added, and stirred at 800 r/min to make a uniform white emulsion. The emulsion was preemulsified for 30 min, stirred in an ice bath for 10 min, deoxidized, and vented with argon gas in the ice bath three times. After deoxidation, persulfate (0.0263 g, 0.01 mmol) was added in the presence of argon gas, and finally, a stopper was tightened. The emulsion was stable and blue in a thermostatic water bath at 35° C., and a conversion rate of styrene monomer was measured to be 97.3% after 4 h, a number average molecular weight $M_n$ of polymer obtained was 442000 g/mol, an absolute weight average molecular weight $M_{w.MALLS}$ was 1220000 g/mol and a branching factor g' was 0.88.

The above results indicate that TDMAMA is capable of copolymerizing with a polymerizing monomer, capable of preparing a branched polymer, and has a high conversion rate of monomer.

Example 5: Emulsion Polymerization Reaction of TDMAMA and TDMAIA with Different Dilute HCl Contents (1) Emulsion Polymerization Reaction of a Functional Monomer TDMAMA A study was carried out with a molar ratio of TDMAMA to dilute HCl at a concentration of 37% being 1:1, 1:0.75, 1:0.50, 1:0.25, i.e., HCl (0.0950 g, 0.96 mmol), (0.0711 g, 0.72 mmol), (0.0472 g, 0.48 mmol), (0.0241 g 0.24 mmol) was weighed and dissolved in deionized water (8 g, 4 $m_{St}$) respectively and TDMAMA (0.3402 g, 0.96 mmol), a functional monomer prepared in Example 1 was added. After stirring and waiting for it to dissolve, mixed water solutions of the functional monomer and hydrochloric acid were recorded as M-HCl, M-0.75 HCl, M-0.50 HCl, M-0.25 HCl respectively, and a corresponding pH of the water solutions were 5.34, 5.64, 6.12, and 6.49, respectively. Styrene (2.0000 g, 2.0002 g, 2.0002 g, 2.0001 g, 0.019 mol, $m_{St}$:$m_{water}$=1:4) was weighed and added respectively and stirred at 800 r/min to make a uniform white emulsion. After being pre-emulsified for 30 min, the emulsion was stirred in an ice bath for 10 min, deoxidized, and vented with argon gas in the ice bath 3 times. After deoxidation, persulfate (0.0261 g, 0.0265 g, 0.0263 g, 0.0260 g, 0.01 mmol) was added in the presence of argon gas, and finally, a stopper was tightened, then a reaction was carried out for 4 h at 25° C. in a thermostatic water bath respectively.

Figure 3:
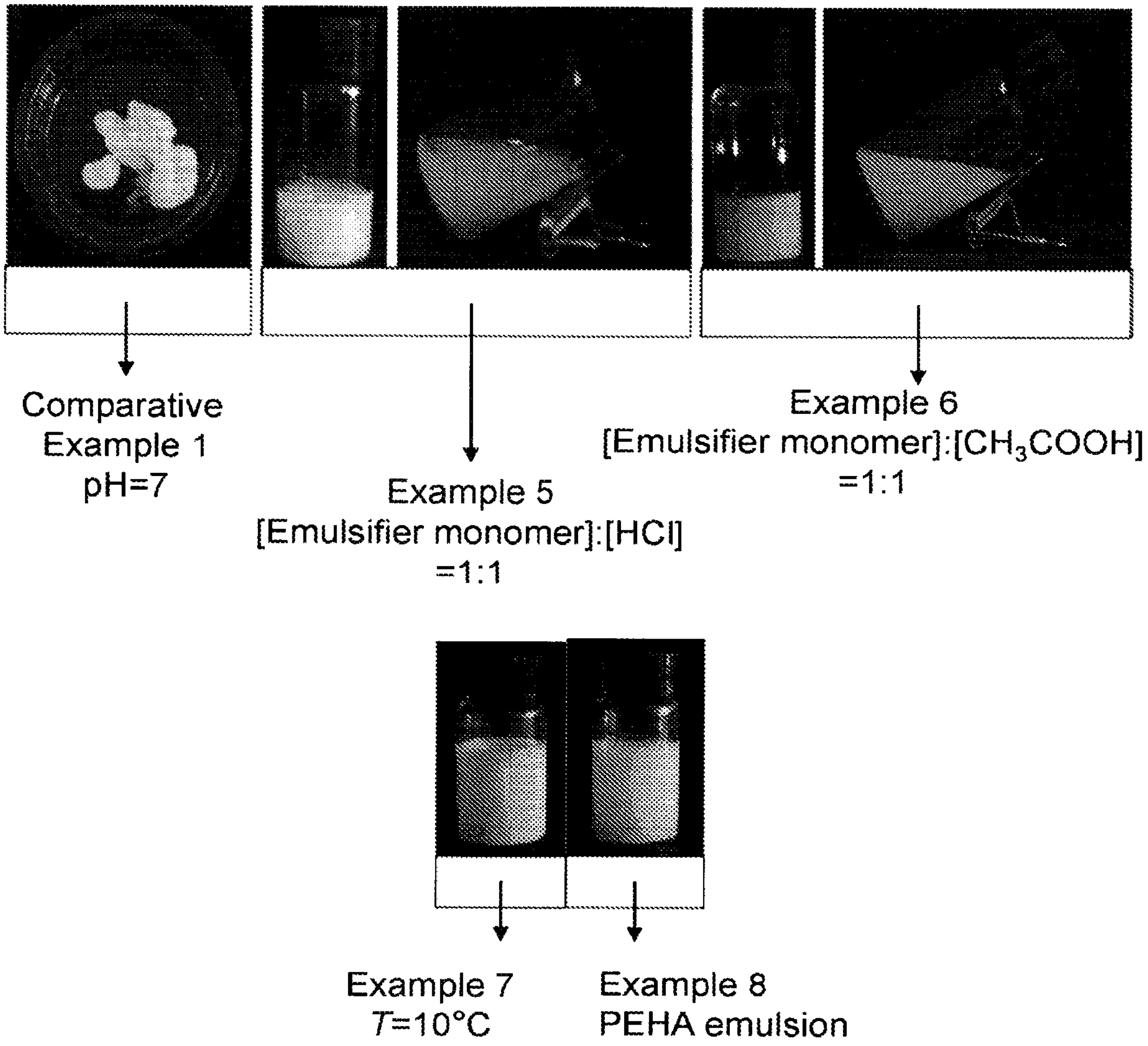
FIG. 3 illustrates an exemplary situation of the emulsion at different $H^+/OH^-$ contents.
Figure 4:
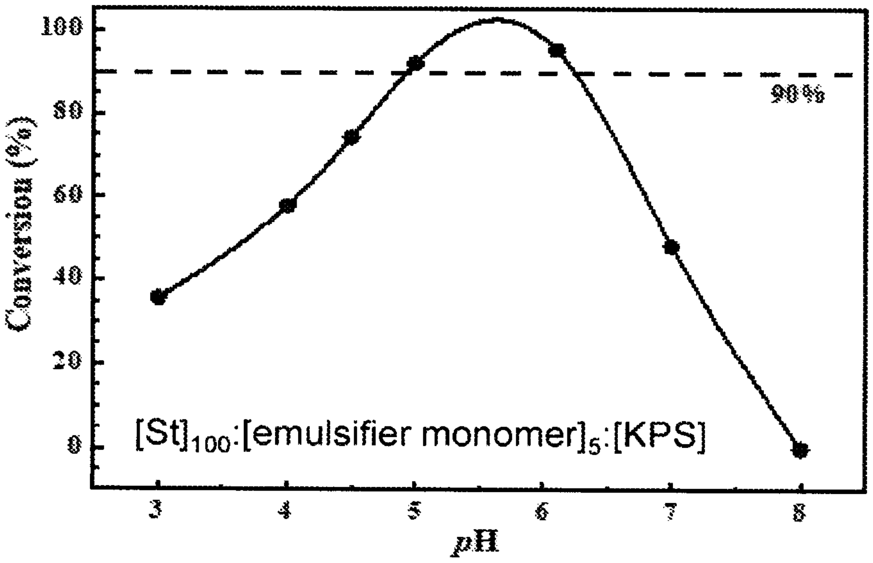
FIG. 4 shows the effect of pH on a conversion rate of a styrene monomer in emulsion polymerization.

When the molar ratio of TDMAMA to HCl was 1:1 and 1:0.75, i.e., the pH of M-HCl and M-0.75HCl were 5.34 and 5.64 respectively, the emulsion stability was good as shown in FIG. 3, and a corresponding conversion rate of monomer were 95% and 97%, and a number average molecular weight $M_n$ of polymer obtained were 660,000 g/mol and 560,000 g/mol, an absolute weight average molecular weight $M_{w.MALLS}$ was 219,000 g/mol and 177,000 g/mol, and a branching factor g' was 0.88 and 0.86 respectively. When the molar ratio of TDMAMA to HCl was 1:0.50, 1:0.25, i.e., the pH of M-0.50HCl and M-0.25HCl were 6.12 and 6.49 respectively, the emulsion stability was decreased, and the conversion rate of monomer was 87% and 80% respectively. As shown in FIG. 4, the number average molecular weight $M_n$ were 630,000 g/mol and 612,000 g/mol respectively, the absolute weight average molecular weight $M_{w.MALLS}$ were 235,000 g/mol and 288,000 g/mol respectively, and the branching factor g' were 0.76 and 0.72 respectively. A particle size of polystyrene prepared by emulsion polymerization at room temperature corresponding to M-HCl, M-0.75HCl, M-0.50HCl, M-0.25HCl were 27.2 nm, 30.0 nm, 30.8 nm, and 64.8 nm respectively, and the emulsion stability of which was M-HCl>M-0.75HCl>M-0.50HCl>M-0.25, with a corresponding pH gradually increased. When pH>6.50, it is easy to produce flocculation and the conversion rate of monomer is relatively low, and when pH<6.50, the emulsion is stable and blue (as shown in the FIG. 3).

(2) Emulsion Polymerization Reaction of Functional Monomer TDMAIA

A study was carried out with a molar ratio of TDMAIA to dilute HCl at a concentration of 37% being 1:1, 1:0.75, 1:0.50, 1:0.25, i.e., dilute HCl at a concentration of 37% was weighed (0.0951 g, 0.96 mmol), (0.0716 g, 0.72 mmol), (0.0471 g, 0.48 mmol), (0.0245 g, 0.24 mmol) and were dissolved in deionized water (8 g, 4 $m_{St}$), a functional monomer TDMAIA (0.3505 g, 0.96 mmol) prepared in Example 1 was added, and when it was dissolved, pH corresponding to a mixed water solution of TDMAIA and HCl was measured to be 6.05, 6.16, 6.52, and 6.71 respectively. Styrene (2.0002 g, 2.0003 g, 2.0001 g, 2.0003 g, 0.019 mol, $m_{St}$:$m_{water}$=1:4) was weighed and stirred at 800 r/min to make a uniform white emulsion and the emulsion was pre-emulsified for 30 min. After being pre-emulsified, it was stirred in an ice bath for 10 min, deoxidized, and vented with argon gas in the ice bath three times. After deoxidation, persulfate (0.0260 g, 0.0263 g, 0.0261 g, 0.0264 g, 0.01 mmol) was added in the presence of argon gas, and finally, a stopper was tightened, and a reaction was carried out for 4 h at 25° C. in a thermostatic water bath respectively.

When the molar ratio of TDMAIA to HCl was 1:1, 1:0.75, 1:0.50, 1:0.25, a corresponding particle size of polystyrene prepared by emulsion polymerization at room temperature was 42.2 nm, 44.7 nm, 48.3 nm and 84.4 nm respectively. When the molar ratio of TDMAIA to HCl was 1:1 and 1:0.75, the conversion rate of monomer was 96.1% and 94.3%, the number average molecular weight $M_n$ was 480,000 g/mol and 220,000 g/mol, the absolute weight average molecular weight $M_{w.MALLS}$ was 630,000 g/mol and 550,000 g/mol, and the branching factor g' was 0.78 and 0.80 respectively. When the molar ratio of TDMAIA to HCl was 1:0.50 and 1:0.25, the emulsion stability was decreased, and it was easy to produce flocculation, and the conversion rate of monomer was reduced to 79.1% and 53.0% respectively, and the number average molecular weight $M_n$ was 286000 g/mol and 235000 g/mol, and the absolute weight average molecular weight $M_{w.MALLS}$ was 1890000 g/mol and 235000 g/mol respectively, and the branching factor g' was 0.88 and 0.76 respectively.

The two reactive $H^+/OH^-$ responsive functional monomers in the method of the present disclosure can regulate the emulsion polymerization by adjusting an $H^+/OH^-$ content in the emulsion polymerization, so the emulsion remains stable and undergoes polymerization under a condition of a high $H^+$ concentration, and the emulsion flocculates and the reaction terminates under a condition of a high $OH^-$ concentration. Moreover, the $H^+/OH^-$ responsive functional monomer has a tertiary amine structure, and when a molar ratio of the tertiary amine structure to $H^+$ is between 1:0.25~1:1.0 (5.0≤pH<7.0), it may initiate an emulsion polymerization reaction with an oxidizing agent at room temperature (5~35° C.) and achieve a high conversion rate and high molecular weight in a short time.

Example 6: Emulsion Polymerization Reaction of TDMAMA and TDMAIA with Different Glacial Acetic Acid Contents (1) Emulsion Polymerization Reaction of a Functional Monomer TDMAMA $CH_3COOH$ (0.0571 g, 0.96 mmol), (0.0433 g, 0.72 mmol), (0.0288 g, 0.48 mmol), (0.0145 g, 0.24 mmol) was weighed and dissolved in deionized water (8 g, 4 $m_{St}$), and a functional monomer TDMAMA (0.3402 g, 0.96 mmol) was added, then stirred to be dissolved, and a pH corresponding to a mixed water solution of functional monomer and acetic acid was 5.76, 6.08, 6.32, and 6.50 respectively. Styrene (2.0008 g, 2.0010 g, 2.0005 g, 2.0006 g, 0.019 mol, $m_{St}$:$m_{water}$=1:4) was weighed and stirred at 800 r/min to make a uniform white emulsion, then the white emulsion was pre-emulsified for 30 min. After being pre-emulsified, it was stirred in an ice bath for 10 min, deoxidized, and vented with argon gas in the ice bath three times. After deoxidation, persulfate (0.0521 g, 0.0522 g, 0.0520 g, 0.0525 g, 0.19 mmol) was added in the presence of argon gas, and finally, a stopper was tightened, and a reaction was carried out for 8 h at 25° C. in a thermostatic water bath respectively.

When a molar ratio of the functional monomer TDMAMA to $CH_3COOH$ was 1:1, 1:0.75, 1:0.50, and 1:0.25, a corresponding particle size of polystyrene obtained by the emulsion polymerization reaction was 34.1 nm, 40.6 nm, 42.6 nm, and 72.3 nm respectively, When the molar ratio of the functional monomer TDMAMA to $CH_3COOH$ was 1:1, the emulsion was stable and blue (as shown in FIG. 3). When the molar ratio of TDMAMA to $CH_3COOH$ was 1:1 and 1:0.75, a conversion rate of monomer was 99.0% and 94.1%, a number average molecular weight $M_n$ was 210,000 g/mol and 170,000 g/mol respectively, and an absolute weight average molecular weight $M_{w.MALLS}$ was 265,000 g/mol and 18,800,000 g/mol respectively, and a branching factor g' was 0.80 and 0.82 respectively. When the molar ratio of TDMAMA to $CH_3COOH$ was 1:0.50 and 1:0.25, the emulsion stability decreased, and the conversion rate of monomer was 83.4% and 76.1% respectively, and the number average molecular weight $M_n$ was 193000 g/mol and 167000 g/mol respectively, and the absolute weight average molecular weight $M_{w.MALLS}$ was 1550000 g/mol and 1520000 g/mol respectively, and the branching factor g' was 0.87 and 0.85 respectively.

(2) Emulsion Polymerization Reaction of a Functional Monomer TDMAIA $CH_3COOH$ (0.1151 g, 1.92 mmol), (0.0866 g, 1.44 mmol), (0.0577 g, 0.96 mmol), and (0.0291 g, 0.48 mmol) was weighed and dissolved in deionized water (8 g, 4 $m_{St}$), and an $H^+/OH^-$-responsive functional monomer TDMAIA (0.7103 g, 1.92 mmol) was added, TDMAIA and $CH_3COOH$ were mixed to form a water solution, and a pH corresponding to the water solution was 6.01, 6.20, 6.61, and 6.75 respectively, and styrene was weighed (2.0002 g, 2.0003 g, 2.0001 g, 2.0003 g, 0.019 mol, mSt:mwater=1:4) and stirred at 800 r/min to make a uniform white emulsion, then the emulsion was pre-emulsified for 30 m. After being pre-emulsified, it was stirred in an ice bath for 10 min, deoxidized, and vented with argon gas in the ice bath three times. After deoxidation, persulfate (0.0521 g, 0.019 mmol) was added in the presence of argon gas, and finally, a stopper was tightened, and a reaction was carried out for 4 h at 25° C. in a thermostatic water bath.

A corresponding particle size of polystyrene obtained by emulsion polymerization reaction was 34.0 nm, 41.8 nm, 47.7 nm, and 69.9 nm when a molar ratio of TDMAIA to $CH_3COOH$ was 1:1, 1:0.75, 1:0.50 and 1:0.25 respectively. When the molar ratio of TDMAIA to $CH_3COOH$ was 1:1 and 1:0.75, a conversion rate of monomer was 96.2% and 91.1%, respectively, and a number average molecular weight $M_n$ of polystyrene was 485,000 g/mol and 362,000 g/mol respectively, and an absolute weight average molecular weight $M_{w.MALLS}$ was 890,000 g/mol and 630,000 g/mol respectively, and a branching factor g' was 0.56 and 0.49, respectively. When the molar ratio of TDMAIA to $CH_3COOH$ was 1:0.50 and 1:0.25, the emulsion stability decreased, the conversion rate of monomer was 75.3% and 51.2%, the number average molecular weight $M_n$ was 333000 g/mol and 274000 g/mol respectively, and the absolute weight average molecular weight $M_{w.MALLS}$ was 1280000 g/mol and 1330000 g/mol respectively, and the branching factor g' was 0.47 and 0.50 respectively.

Example 7: Emulsion Polymerization Reaction at Low Temperature (1) Emulsion Polymerization Reaction of a Functional Monomer TDMAMA at Low Temperature $CH_3COOH$ (0.05701 g, 0.96 mmol) was weighed and dissolved in deionized water (8.0010 g, 4 $m_{St}$), and an $H^+/OH^-$ responsive functional monomer TDMAMA (0.3401 g, 0.96 mmol) was added and stirred until it was dissolved, and a corresponding pH of a solution was measured to be 6.03. Styrene (2.0010 g, 0.019 mol) was weighed and stirred at 800 r/min to make a uniform white emulsion, and the emulsion was pre-emulsified for 30 min. After being pre-emulsified, it was stirred in an ice bath for 10 min, deoxidized, and vented with argon gas in the ice bath three times. After deoxidation, persulfate (0.0521 g, 0.19 mmol) was added in the presence of argon gas, and finally, a stopper was tightened and a reaction was carried out at 10° C. for 6 h in a thermostatic water bath. The emulsion was stable and blue during the reaction, as shown in FIG. 3. The monomer conversion rate of styrene was 95.74%, the number average molecular weight $M_n$ was 580,000 g/mol, the absolute weight average molecular weight $M_{w.MALLS}$ was 288,000 g/mol, and the branching factor g' was 0.79, as measured by gas chromatography.

(2) Emulsion Polymerization Reaction of a Functional Monomer TDMAIA at Low temperature $CH_3COOH$ (0.05700 g, 0.96 mmol) was weighed and dissolved in deionized water (8.0004 g, 4 $m_{St}$), and $H^+/OH^-$ responsive emulsifier monomer TDMAIA (0.3503 g, 0.96 mmol) was added, and stirred to be dissolved, and the corresponding pH of the solution was measured to be 6.03 respectively, and styrene (2.0002 g 0.019 mol) was weighed, stirred at 800 r/min to make a uniform white emulsion and the emulsion was pre-emulsified for 30 min. After being pre-emulsified, it was stirred in an ice bath for 10 min, deoxidized, and vented with argon gas in the ice bath for 3 times. After deoxidation, persulfate (0.052 g, 0.019 mmol) was added in the presence of argon gas, and finally, a stopper was tightened and a reaction was carried out at 5° C. for 6 h in a thermostatic water bath. The emulsion was stable and blue during the reaction. A conversion rate of monomer of styrene was 92.61% as measured by gas chromatography, a number average molecular weight $M_n$ was 610000 g/mol, an absolute weight average molecular weight $M_{w.MALLS}$ was 3010000 g/mol, and a branching factor g' was 0.81.

Example 8: Emulsion Polymerization Reaction of TDMAMA with Different Vinyl Monomers Dilute HCl (0.2180 g, 2.2 mmol) with a concentration of 37% was weighed and dissolved in deionized water (5.20 g, $m_{monomer}$:$m_{water}$=9:11), and an $H^+/OH^-$ responsive functional monomer TDMAMA (0.7801 g, 2.2 mmol) was added, stirred to dissolve, and a corresponding pH of a solution was measured to be 6.01. Acrylic acid (0.1100 g, 1.5 mmol), hydroxyethyl acrylate (0.1000 g, 0.77 mmol), ethyl methacrylate (0.2202 g, 2.2 mmol), and isooctyl acrylate (4.0001 g, 0.02 mol) was weighed and stirred to make a uniform white emulsion at 800 r/min, and the emulsion was pre-emulsified for 30 min. After being pre-emulsified, it was stirred in an ice bath for 10 min, deoxidized, and vented with argon gas in the ice bath three times. After deoxidation, ammonium persulfate (0.0490 g, 0.21 mmol) was added in the presence of argon gas, and finally, a stopper was tightened and a reaction was carried out at 25° C. for 8 h in a thermostatic water bath. The emulsion was stable and blue during the reaction as shown in FIG. 3. A conversion rate of isooctyl acrylate was 96.7%, a conversion rate of acrylic acid was 93.5%, a conversion rate of ethyl methacrylate was 95.3%, a conversion rate of hydroxyethyl acrylate was 98.5% as measured by gas chromatography, a number average molecular weight $M_n$ was 145000 g/mol, an absolute weight-average molecular weight $M_{w.MALLS}$ was 431000 g/mol, and a branching factor g' was 0.43.

Example 9: Emulsion Polymerization Reaction

Dilute HCl (0.1586 g, 1.6 mmol) at a concentration of 37% was weighed and dissolved in deionized water (8.0002 g, 4 $m_{n-BA}$), and an $H^+/OH^-$ responsive functional monomer TDMAMA (0.5701 g, 1.6 mmol) was added, stirred and left to dissolve, and a pH was measured to be 6.11. Butyl acrylate (2.0 g. 0.016 mol) was weighed and stirred at a certain speed to make a uniform white emulsion and the emulsion was pre-emulsified for 30 min. After being pre-emulsified, it was stirred in an ice bath for 10 min, deoxidized, and vented with argon gas in the ice bath 3 times.

After deoxidation, an initiator, persulfate (0.042 g, 0.16 mmol) was added in the presence of argon gas, and finally, a stopper was tightened and a reaction was carried out at 25° C. for 8 h in a thermostatic water bath, and the emulsion was stable and blue during the reaction. After 8 h of reaction, a conversion rate of butyl acrylate was measured to be 89.1%. In the emulsion of the reaction, 3 mL of NaOH solution (a concentration of 1 mol/L) was added, then the emulsion was broken, and the reaction terminated, at this time, a pH of the emulsion was 8.00, and the NaOH solution was further added dropwise, then a polymer was precipitated out of the emulsion.

Comparative Example 1: Emulsion Polymerization Reaction

A functional monomer TDMAMA (0.3402 g, 0.96 mmol) was weighed and added to deionized water (8 g, 4 $m_{St}$) at a pH of 7 and stirred, and when it was dissolved, a pH of a solution was measured to be 7. Styrene (2.0002 g, 0.019 mol) was weighed, and it was stirred to make a uniform white emulsion at 800 r/min, and the emulsion was pre-emulsified for 30 min. After being pre-emulsified, it was stirred in an ice bath for 10 min, deoxidized, and vented with argon gas in the ice bath three times. After deoxidation, persulfate (0.0521 g, 0.19 mmol) was added in the presence of argon gas, and finally, a stopper was tightened and a reaction was carried out at 25° C. for 8 h in a thermostatic water bath. During the reaction, it was observed that the emulsion was unstable and flocculated as shown in FIG. 3. When there was no free $H^+$ in the emulsion, the emulsion was unstable, and the functional monomer TDMAMA may only be used as a reducing agent and polymerizing monomer, and may not carry out a stable emulsion polymerization reaction without adding an additional emulsifier.

Comparative Example 2

An $H^+/OH^-$ responsive functional monomer TDMAMA (0.3411 g, 1 mmol) was weighed, dissolved in deionized water (8.0321 g, 4 $m_{St}$) at a pH of 1.0, and stirred to dissolve, and then styrene (St) (2.0121 g, 0.02 mol) was weighed and stirred to make a uniform white emulsion at 800 r/min, then the emulsion was pre-emulsified for 30 min. After being pre-emulsified, it was stirred in an ice bath for 10 min, deoxidized, and vented with argon gas in the ice bath three times. After deoxidation, persulfate (0.0521 g, 0.2 mmol) was added in the presence of argon gas, and finally, a stopper was tightened, a reaction was carried out at 25° C. for 6 h in a thermostatic water bath, the emulsion is stable and not blue, the emulsion has not reacted, then the functional monomer TDMAMA is only used as a monomer.

Comparative Example 3

An $H^+/OH^-$ responsive functional monomer TDMAMA (0.3413 g, 1 mmol) was weighed, dissolved in deionized water (8.0325 g, 4 $m_{St}$) at a pH of 3.0, and stirred to dissolve, then styrene (St) (2.0121 g, 0.02 mol) was weighed and stirred at 800 r/min to make a uniform white emulsion, and the emulsion was pre-emulsified for 30 min. After being pre-emulsified, it was stirred in an ice bath for 10 min, deoxidized, and vented with argon gas in the ice bath three times. After deoxidation, persulfate (0.05212 g, 0.2 mmol) was added in the presence of argon gas, and finally, a stopper was tightened, and a reaction was carried out for 6 h at 25° C. in a thermostatic water bath, and the emulsion was blue, but the emulsion stability was not good, and a conversion rate of styrene was 35.7%, a number average molecular weight $M_n$ was 66,000 g/mol, an absolute weight-average molecular weight $M_{w.MALLS}$ was 1420000 g/mol, and a branching factor g' is 1. Polystyrene formed is a linear polymer, DMAMA is non-reductive in an emulsion at a pH of 3.0, and may only be used as an emulsifier and monomer, but the emulsion stability is not good.

Comparative Example 4

An $H^+/OH^-$ responsive functional monomer TDMAMA (0.3411 g, 1 mmol) was weighed, dissolved in deionized water (8.0323 g, 4 $m_{St}$) at a pH of 5.0, and stirred to dissolve, then styrene (St) (2.0120 g, 0.02 mol) was weighed and stirred at 800 r/min to make a uniform white emulsion, then the emulsion was pre-emulsified for 30 min. After being pre-emulsified, it was stirred in an ice bath for 10 min, deoxidized, and vented with argon gas in the ice bath three times. After deoxidation, persulfate (0.0520 g, 0.2 mmol) was added in the presence of argon gas, and finally, a stopper was tightened, and a reaction was carried out at 25° C. for 6 h in a thermostatic water bath, and a conversion rate of styrene was 92.1%, a number average molecular weight $M_n$ was 880,000 g/mol, an absolute weight average molecular weight $M_{w.MALLS}$ was 207,000 g/mol, and a branching factor g' was 0.96. Polystyrene formed is a linear polymer, TDMAMA is non-reductive in an emulsion at a pH of 5.0, and may be only used as an emulsifier and monomer.

What is claimed is:

1. A method of preparing a polymer by using a functional monomer, comprising:

dissolving the functional monomer in a water solution containing a pH regulating agent to obtain a mixed solution;

controlling a pH of the mixed solution;

adding a vinyl monomer and stirring to form an emulsion; and adding an oxidizing agent to carry out emulsion polymerization and obtaining the polymer, wherein a structure of the functional monomer is shown as:

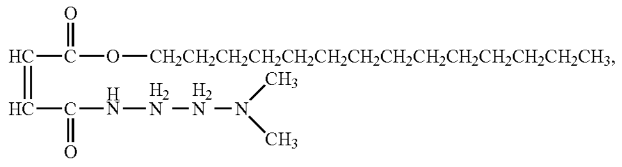

or

-continued

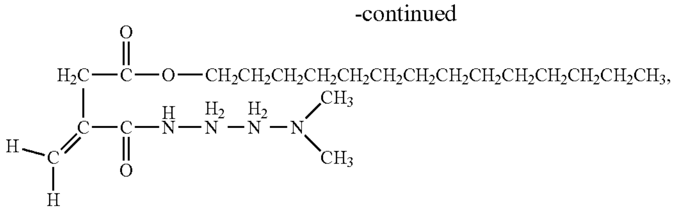

wherein when pH<3.0, the functional monomer is used as an emulsifier;

when 3.0≤pH<5.0, the functional monomer is used as an emulsifier and a polymerizing monomer;

when 5.0≤pH<7.0, the functional monomer is used as an emulsifier, polymerizing monomer and reducing agent;

when 7.0≤pH<8.0, the functional monomer is used as a reducing agent and a polymerizing monomer; and when pH≥8.0, the functional monomer is used only as an emulsion breaker.

2. The method according to claim 1, wherein when 5.0≤pH<7.0, an emulsion polymerization process of the functional monomer includes:

weighing the pH regulating agent and dissolving it in water, adding the functional monomer, and stirring it until it is dissolved to obtain the mixed solution;

controlling the pH of the mixed solution to 5.0≤pH<7.0 through an amount of acid, adding the vinyl monomer and stirring to make it a uniform white emulsion; after completing the deoxidation, in the presence of argon, adding the oxidizing agent to constitute a redox initiation system, wherein the emulsion is stable and blue; and performing the emulsion polymerization at room temperature; adjusting the pH≥8.0 to terminate the emulsion polymerization, and collecting the polymer by separating and precipitating the polymer.

3. The method according to claim 1, wherein the pH regulating agent is one of hydrochloric acid, glacial acetic acid, sodium hydroxide, or sodium bicarbonate.

4. The method according to claim 1, wherein a molar ratio of the functional monomer to $H^+$ is 1:(0.25-1.0).

5. The method according to claim 1, wherein a molar ratio of the functional monomer to the vinyl monomer is (3-5):100.

6. The method according to claim 1, wherein the vinyl monomer is styrene monomer, methacrylate monomer, or acrylic monomer.

7. The method according to claim 2, wherein the oxidizing agent is persulfate.

8. The method according to claim 2, wherein a molar ratio of the functional monomer to the oxidizing agent is (5-10):1.

9. The method according to claim 2, wherein the emulsion polymerization time is 4-8 h and the emulsion polymerization is performed at room temperature of 5° C.-35° C.

* * * * *